US006318369B1

(12) United States Patent
Gregory

(10) Patent No.: US 6,318,369 B1
(45) Date of Patent: Nov. 20, 2001

(54) EYE EAR AND RESPIRATION PROTECTION APPARATUS

(76) Inventor: Kenneth M. Gregory, 414 Armour Cir., Atlanta, GA (US) 30324

( * ) Notice: Subject to any disclaimer, the term of this patent is extended or adjusted under 35 U.S.C. 154(b) by 0 days.

(21) Appl. No.: 09/261,312

(22) Filed: Mar. 2, 1999

Related U.S. Application Data

(60) Provisional application No. 60/076,929, filed on Mar. 5, 1998.

(51) Int. Cl.[7] ..................... A61F 11/00

(52) U.S. Cl. ..................... 128/857; 128/858; 128/201.22

(58) Field of Search ..................... 128/857, 858, 128/866, 868, 201.22, 201.23, 201.24, 206.21, 206.24, 206.23, 205.27, 206.13; 2/410, 6.2, 6.3, 417, 421, 423, 424, 15, 909

(56) References Cited

U.S. PATENT DOCUMENTS

| | | | | |
|---|---|---|---|---|
| 2,379,493 | | 7/1945 | Morehouse . | |
| 2,861,567 | | 11/1958 | Queter et al. . | |
| 3,108,282 | * | 10/1963 | Rehman et al. | 128/857 |
| 4,259,747 | * | 4/1981 | Taesler et al. | 2/6 |
| 4,352,353 | | 10/1982 | Bolton et al. . | |
| 4,402,316 | * | 9/1983 | Gadberry | 128/201.15 |
| 4,648,138 | * | 3/1987 | Brigden et al. | 2/6 |
| 5,054,480 | * | 10/1991 | Bare et al. | 128/201.25 |
| 5,069,205 | * | 12/1991 | Urso | 128/201.24 |
| 5,252,069 | * | 10/1993 | Lamb et al. | 2/209 |
| 5,278,999 | * | 1/1994 | Brown et al. | 2/6.3 |
| 5,483,975 | | 1/1996 | Hirschenbaun . | |
| 5,546,610 | * | 8/1996 | Herzig et al. | 2/423 |
| 5,572,990 | | 11/1996 | Berlin . | |
| 5,603,117 | * | 2/1997 | Hudner, Jr. et al. | 2/6.6 |
| 5,630,412 | * | 5/1997 | Dubruille et al. | 128/206.23 |
| 5,664,566 | * | 9/1997 | McDonald et al. | 128/205.25 |
| 5,694,925 | * | 12/1997 | Reese et al. | 128/206.19 |
| 5,704,073 | * | 1/1998 | Sword et al. | 2/427 |
| 5,722,091 | * | 3/1998 | Keller et al. | 2/6.3 |
| 5,796,374 | * | 8/1998 | Cone et al. | 345/8 |
| 5,941,245 | * | 8/1999 | Hannah et al. | 128/207.11 |
| 6,085,748 | * | 7/2000 | Sword et al. | 128/206.23 |

* cited by examiner

*Primary Examiner*—John G. Weiss
*Assistant Examiner*—Teena Mitchell

(57) ABSTRACT

An eye, ear, and respiration protection apparatus includes a respirator assembly which includes a nose and mouth mask, an air filter element connected to the nose and mouth mask, and an air flow valve connected to the nose and mouth mask. An attachment wire is connected to the nose and mouth mask, and an eye goggle assembly is connected to the attachment wire. Ear protector attachment means are connected to the nose and mouth mask, and an ear protector assembly is connected to the ear protector attachment means. When a wearer wears the eye, ear, and respiration protection apparatus of the invention, the wearer's respiratory tract is protected from airborne materials, the wearer's eyes are protected from airborne materials and radiation, and the wearer's ears are protected from airborne materials and loud noises. The ear protector assembly includes first and second ear cover support strut assemblies connected to the ear protector attachment wire. Ear cover assemblies are connected to ear cover support strut assemblies. An overhead band is connected between the first ear cover assembly and the second ear cover assembly and is pivotally connected to thereto to provide fore and aft adjustment. The overhead band furthermore is slidingly and lockingly adjustable relative to the ear cover assemblies to provide optimum comfort and fit to an individual wearer. With another embodiment of the invention, both an overhead band and a rearward headband are provided, and a pair of band locking units lock the headbands in adjusted positions.

11 Claims, 6 Drawing Sheets

EYE EAR AND RESPIRATION PROTECTION APPARATUS

CROSS-REFERENCE TO RELATED APPLICATION

This application claims priority based upon my prior copending Provisional Application Ser. No. 60/076,929, filed Mar. 5, 1998.

BACKGROUND OF THE INVENTION

1. Field of the Invention

The present invention relates generally to masks used by persons to protect their breathing passages from a contaminating atmosphere and, more particularly, to such masks which also provide eye protection.

2. Description of the Prior Art

Masks which protect both a wearer's breathing passages and the wearer's eyes are well known in the art. In this respect, throughout the years, a number of innovations have been developed relating to such masks, and the following U.S. patents are representative of some of those innovations: U.S. Pat. Nos. 2,379,493, 2,861,567, 4,352,353, and 5,483,975, 5,572,990. More specifically, U.S. Pat. No. 2,379,493 discloses a breathing mask that protects breathing passages and eyes. In addition, this apparatus also protects the wearer's ears from excessive noise. It is noted that this apparatus also covers a substantial portion of the wearer's forehead and neck, in addition to the wearer's nose, mouth, eyes, and ears. To provide for more extensive ventilation, it would be desirable if an eye, ear, and respiration protection apparatus did not cover substantial portions of the wearer's forehead and neck.

U.S. Pat. No. 2,861,567 discloses a pressurized helmet for aviators. To retain pressure, the head of the wearer is enclosed by the helmet. U.S. Pat. No. 4,352,353 discloses headgear with encloses the entire head of a wearer to protect the wearer's eyes, breathing passages, and ears from toxic substances. U.S. Pat. No. 5,483,975 discloses a device worn by a diver to facilitate equalizing pressure across the eardrum of the diver. With this apparatus, the diver can breath through one's mouth, but cannot breath through one's nose. U.S. Pat. No. 5,572,990 discloses a respiratory mask that covers a wearer's mouth and nose. The device is in helmet form to cover the entire head of the wearer.

Still other features would be desirable in an eye, ear, and respiration protection apparatus. For example, rather than using a helmet motif, it would be desirable if a nose and mouth mask were connected to an ear protector assembly using linear struts. In this regard, it would be desirable if the linear struts between the nose and mouth mask and the ear protector assembly were adjustable to accommodate different size heads. Also, it would desirable if the ear protector assembly were adjustable laterally to accommodate different head sizes. To stabilize the support and positioning the eye, ear, and respiration protection apparatus on a wearer's head, it would be desirable if the apparatus included one headstrap that extends over the wearer's head and includes another headstrap that extends behind the wearer's head. Also, in adjusting the headstraps on a wearer's head, it would be desirable if push buttons locks were provided both to release the headstraps when adjustments are needed and to lock the headstraps after the adjustments have been made.

Thus, while the foregoing body of prior art indicates it to be well known to use masks to protect a wearer's eyes, ears, and breathing passages, the prior art described above does not teach or suggest an eye, ear, and respiration protection apparatus which has the following combination of desirable features: (1) does not cover substantial portions of the wearer's forehead and neck; (2) uses linear struts to connect a nose and mouth mask to an ear protector assembly; (3) provides that the linear struts between the nose and mouth mask and the ear protector assembly are adjustable to accommodate different size heads; (4) provides that the ear protector assembly is adjustable laterally to accommodate different head sizes; (5) includes one headstrap that extends over the wearer's head and includes another headstrap that extends behind the wearer's head; and (6) provides push buttons locks both to release the headstraps when adjustments are needed and to lock the headstraps after the adjustments have been made. The foregoing desired characteristics are provided by the unique eye, ear, and respiration protection apparatus of the present invention as will be made apparent from the following description thereof. Other advantages of the present invention over the prior art also will be rendered evident.

SUMMARY OF THE INVENTION

To achieve the foregoing and other advantages, the present invention, briefly described, provides an eye, ear, and respiration protection apparatus which includes a respirator assembly which includes a nose and mouth mask, an air filter element connected to the nose and mouth mask, and an air flow valve connected to the nose and mouth mask. Eye protector attachment means are connected to the nose and mouth mask, and an eye goggle assembly is connected to the eye protector attachment means. Ear protector attachment means are connected to the nose and mouth mask, and an ear protector assembly is connected to the ear protector attachment means. When a wearer wears the eye, ear, and respiration protection apparatus of the invention, the wearer's respiratory tract is protected from airborne materials, the wearer's eyes are protected from airborne materials and radiation, and the wearer's ears are protected from airborne materials and loud noises.

The eye protector attachment means and the ear protector attachment means are comprised of a single attachment wire connected to the nose and mouth mask. The eye goggle assembly includes goggle connector portions connected to the attachment wire. The goggle connector portions are rotatable around the attachment wire.

The ear protector assembly includes a first ear cover support strut assembly connected to the ear protector attachment. A first ear cover assembly is connected to the first ear cover support strut assembly. A second ear cover support strut assembly is connected to the ear protector attachment. A second ear cover assembly is connected to the second ear cover support strut assembly.

An overhead band is connected between the first ear cover assembly and the second ear cover assembly. The overhead band is pivotally connected to the first ear cover assembly and the second ear cover assembly to provide fore and aft adjustment. The overhead band furthermore is slidingly and lockingly adjustable relative to the ear cover assemblies to provide optimum comfort and fit to an individual wearer.

A first tension spring is connected to both the ear protector attachment and the first ear cover support strut assembly for urging the first ear cover support strut assembly towards a wearer's head. A second tension spring is connected to both the ear protector attachment and the second ear cover support strut assembly for urging the second ear cover support strut assembly towards the wearer's head. Each of the first ear cover support strut assembly and the second ear cover support strut assembly includes a first telescopic strut member connected to the ear protector attachment and a second telescopic strut member is connected between the first telescopic strut member and one of the ear cover assemblies. A strut lock member is received in the second telescopic strut member and is used for locking the first telescopic strut member and the second telescopic strut member in a selected longitudinal adjustment.

With another embodiment of the invention, both a overhead band and a rearward headband are provided. The overhead band includes a band ring end attached to the exterior of a first of a pair of band locking units and includes a serrated portion received in an interior portion of a second of the pair of band locking units. In like manner, the rearward headband includes a band ring end attached to the exterior of the second of the pair of band locking units and includes a serrated portion received in the interior of the first of the pair of band locking units. With this arrangement of the overhead band, the rearward headband, and the band locking units, the wearer has independent control of the tension and orientation angle of each of the overhead band and the rearward headband.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining at least two preferred embodiments of the invention in detail, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

It is therefore an object of the present invention to provide a new and improved eye, ear, and respiration protection apparatus which has all of the advantages of the prior art and none of the disadvantages.

It is another object of the present invention to provide a new and improved eye, ear, and respiration protection apparatus which may be easily and efficiently manufactured and marketed.

It is a further object of the present invention to provide a new and improved eye, ear, and respiration protection apparatus which is of durable and reliable construction.

An even further object of the present invention is to provide a new and improved eye, ear, and respiration protection apparatus which is susceptible of a low cost of manufacture with regard to both materials and labor, and which accordingly is then susceptible of low prices of sale to the consuming public, thereby making such eye, ear, and respiration protection apparatus available to the buying public.

Still yet a further object of the present invention is to provide a new and improved eye, ear, and respiration protection apparatus which does not cover substantial portions of the wearer's forehead and neck Still another object of the present invention is to provide a new and improved eye, ear, and respiration protection apparatus that uses linear struts to connect a nose and mouth mask to an ear protector assembly Yet another object of the present invention is to provide a new and improved eye, ear, and respiration protection apparatus which provides that the linear struts between the nose and mouth mask and the ear protector assembly are adjustable to accommodate different size heads Even another object of the present invention is to provide a new and improved eye, ear, and respiration protection apparatus that provides that the ear protector assembly is adjustable laterally to accommodate different head sizes Still a further object of the present invention is to provide a new and improved eye, ear, and respiration protection apparatus which includes one headstrap that extends over the wearer's head and includes another headstrap that extends behind the wearer's head Yet another object of the present invention is to provide a new and improved eye, ear, and respiration protection apparatus that provides push buttons locks both to release the headstraps when adjustments are needed and to lock the headstraps after the adjustments have been made These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawing wherein.

DESCRIPTION OF THE PREFERRED EMBODIMENT

Figure 1:
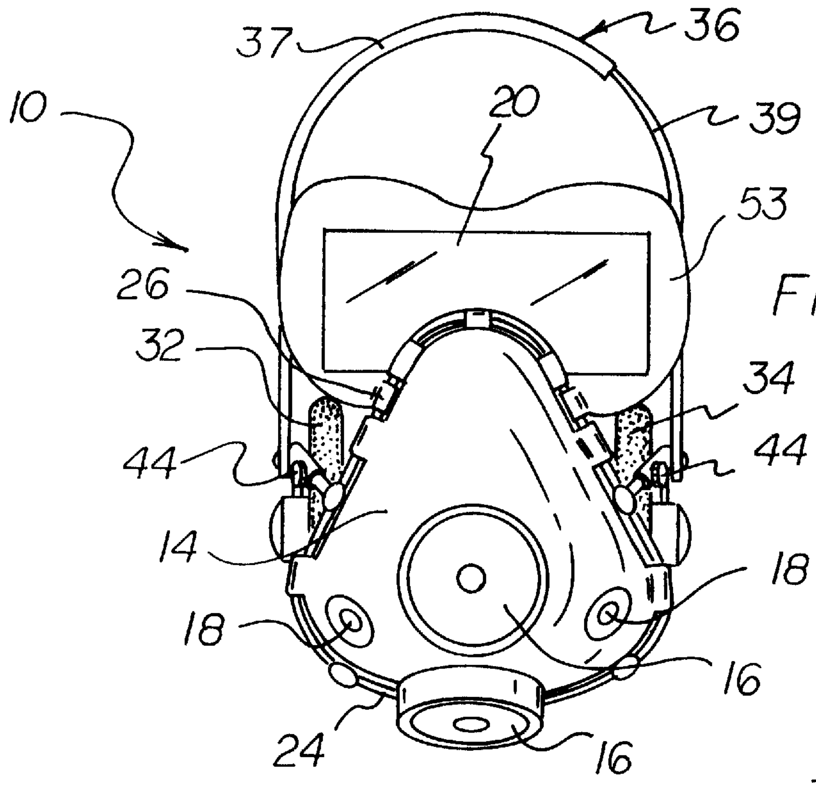
FIG. 1 is a front view showing a first embodiment of the eye, ear, and respiration protection apparatus of the invention.
Figure 2:
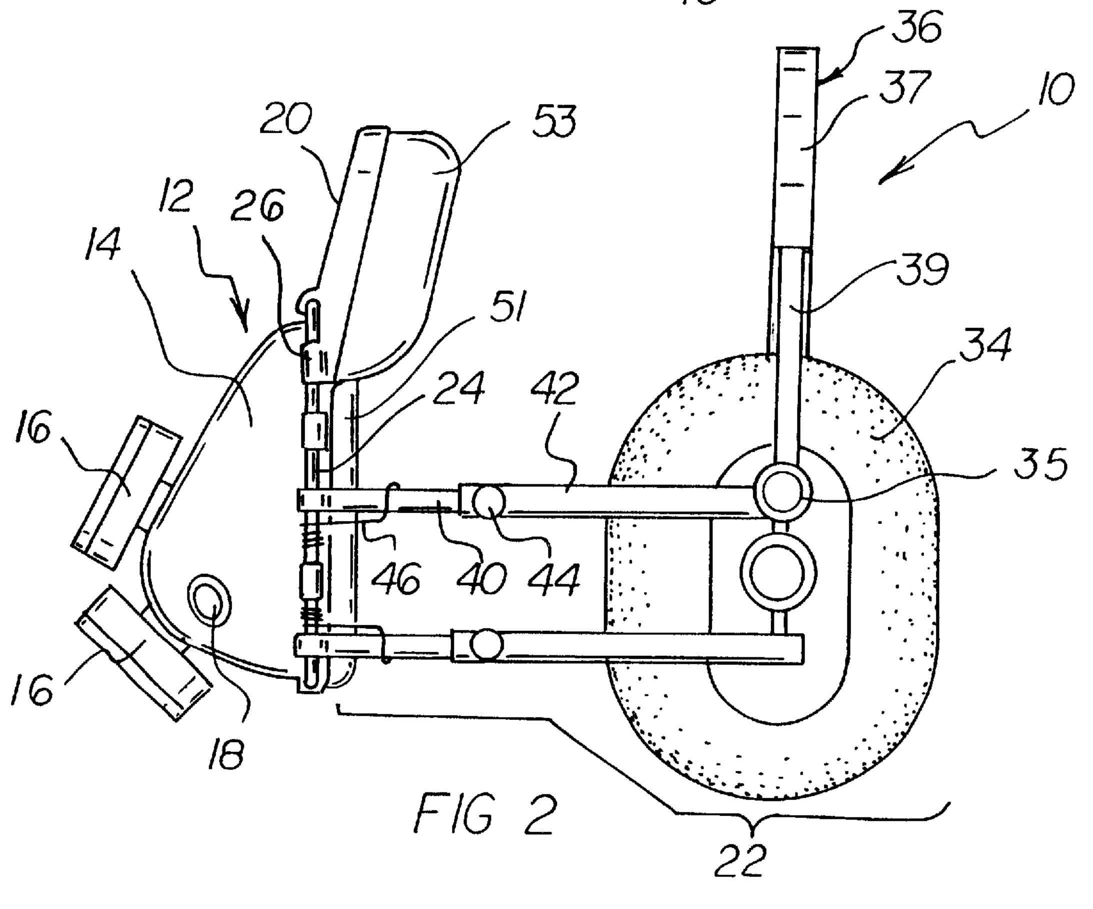
FIG. 2 is a side view of the embodiment of the eye, ear, and respiration protection apparatus shown in FIG. 1.
Figure 3:
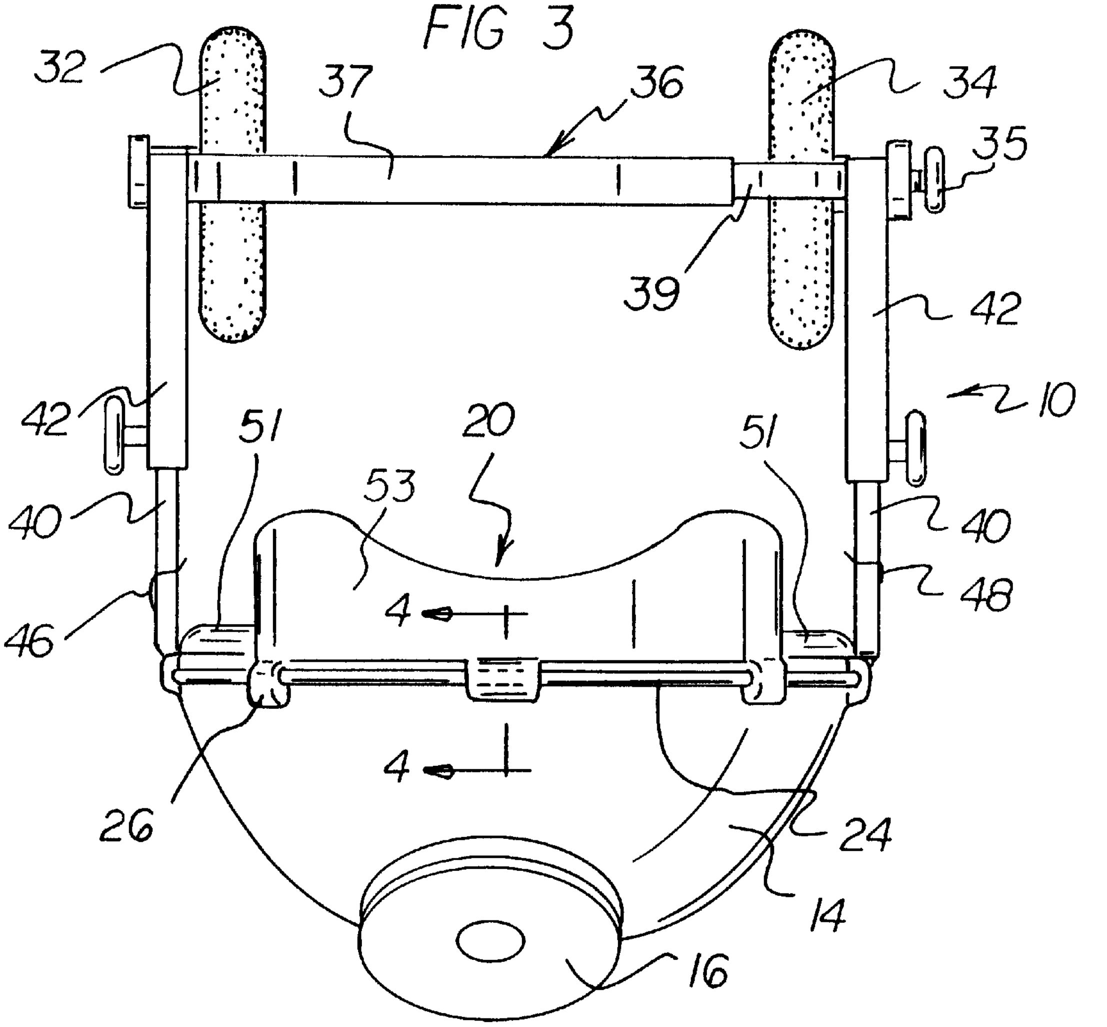
FIG. 3 is a top view of the embodiment of the eye, ear, and respiration protection apparatus shown in FIG. 1.
Figure 4:
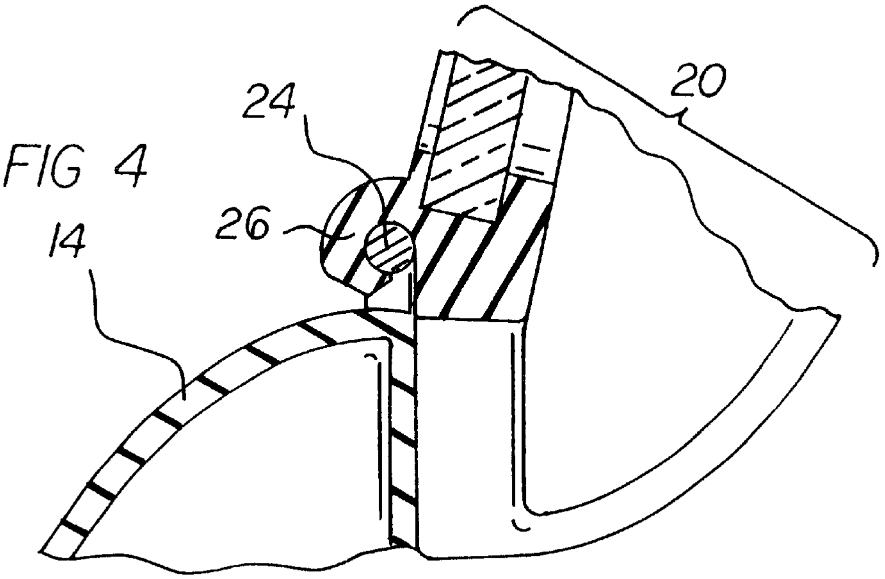
FIG. 4 is an enlarged partial cross-sectional view of a portion of the embodiment of the invention shown in FIG. 3 taken along line 4—4 thereof.
Figure 5:
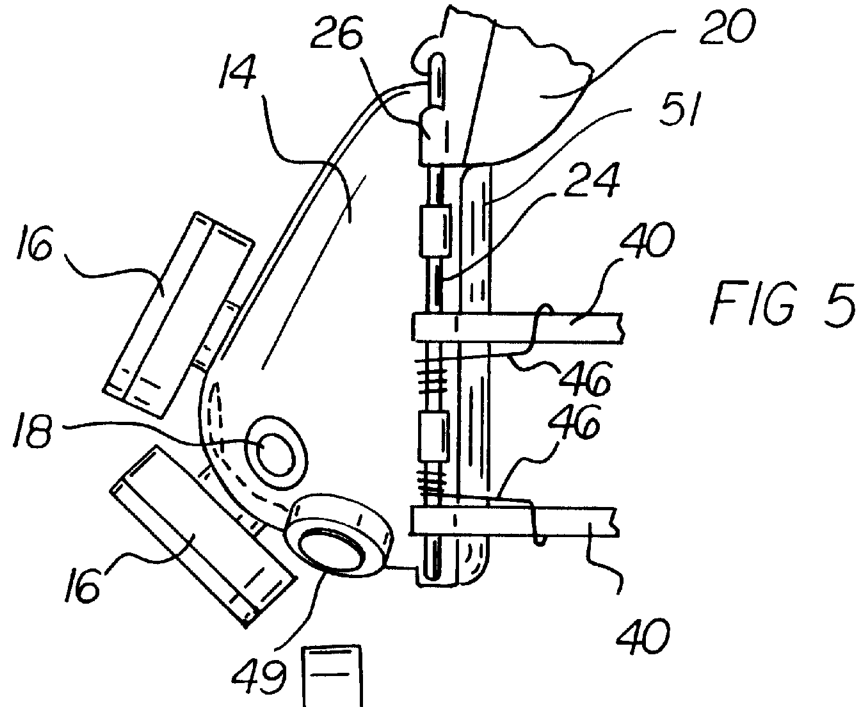
FIG. 5 is an enlarged partial side view of the face protecting portion of the embodiment of the invention shown in FIG. 2.

With reference to the drawings, a new and improved eye, ear, and respiration protection apparatus embodying the principles and concepts of the present invention will be described.

Turning to FIGS. 1–6, there is shown an exemplary embodiment of the eye, ear, and respiration protection apparatus of the invention generally designated by reference numeral 10. In its preferred form, the eye, ear, and respiration protection apparatus 10 includes a respirator assembly 12 which includes a nose and mouth mask 14, an air filter element 16 connected to a filter reception channel in the nose and mouth mask 14, and a one-way air flow or exhaust valve 18 connected to a valve reception channel in the nose and mouth mask 14. Eye protector attachment means are connected to the nose and mouth mask 14, and an eye goggle assembly 20 is connected to the eye protector attachment means. Ear protector attachment means are connected to the nose and mouth mask 14, and an ear protector assembly 22 is connected to the ear protector attachment means. When a wearer wears the eye, ear, and respiration protection apparatus 10 of the invention, the wearer's respiratory tract is protected from airborne materials, the wearer's eyes are protected from airborne materials and radiation, and the wearer's ears are protected from airborne materials and loud noises. Two-way communication between individuals wearing the protection apparatus of the present invention is possible by utilizing conventional electronic communication apparatus (e.g. radio or telephone suitably mounted on the apparatus).

The eye protector attachment means and the ear protector attachment means are comprised of a single attachment wire 24 connected to the nose and mouth mask 14. The eye goggle assembly 20 includes goggle connector portions 26 connected to the attachment wire 24. The goggle connector portions 26 are rotatable around the attachment wire 24.

The ear protector assembly 22 includes a first ear cover support strut assembly connected to the ear protector attachment. A first ear cover assembly 32 is connected to the first ear cover support strut assembly. A second ear cover support strut assembly is connected to the ear protector attachment. A second ear cover assembly 34 is connected to the second ear cover support strut assembly.

Figure 6:
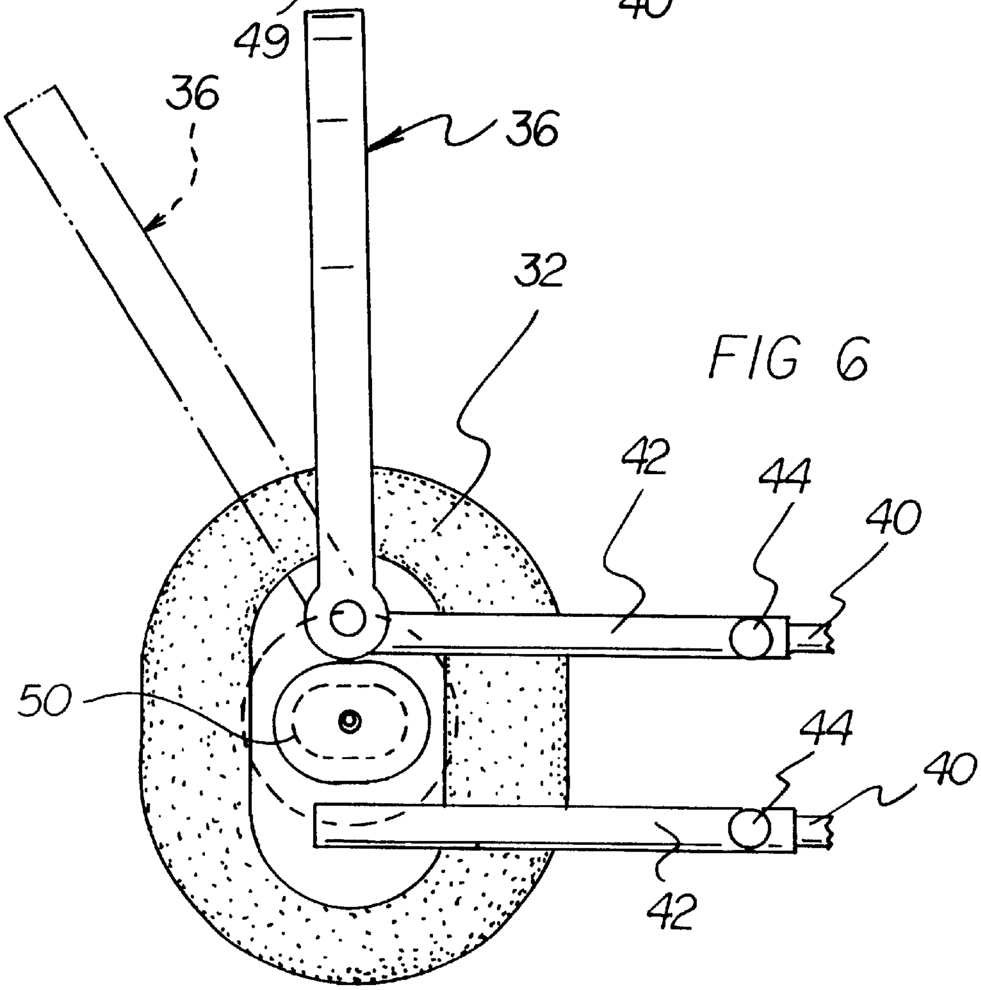
FIG. 6 is an enlarged partial side view of the ear protecting portion of the embodiment of the invention shown in FIG. 2.

An overhead band 36 is connected between the first ear cover assembly 32 and the second ear cover assembly 34. The overhead band 36 is pivotally connected to the first ear cover assembly 32 and the second ear cover assembly 34 to provide fore and aft adjustable movement. Two different orientation angles of the overhead band 36 are shown in FIG. 6. The angle of the overhead band 36 with respect to the first ear cover assembly 32 and the second ear cover assembly 34 can be fixed by using a ratchet assembly.

The overhead band assembly 36 is adjustable to provide optimum comfort and fit to an individual. In this regard, the band assembly 36 includes a locking knob 35 adapted to releasably fix the terminal portion of headband assembly 36 in a preferred selected position. Band assembly 36 may comprise a single one-piece member, or alternatively, may include a first telescopic band member 37 connected to the first ear cover assembly 32, and a second telescopic band member 39 is connected to the second ear cover assembly 34. The first telescopic band member 37 telescopically receives the second telescopic band member 39. The position of the first telescopic band member 37 with respect to the second telescopic band member 39 can be fixed by frictional forces between the first telescopic band member 37 and the second telescopic band member 39. Adjustment of the headband assembly 36 is effected by rotating the locking knob 35 to release the terminal portion and thereby permit sliding movement up or down of the terminal portion relative to ear cover assembly 34 via a conventional ratchet mechanism or the like. The parts may then be locked in the desired position by suitably rotating locking knob 35 to a tightened condition. Where a telescoped headband assembly also is provided, additional fine tuning of headband adjustment may be provided simply by sliding terminal portion relative to band portion 37. It will be appreciated that to reduce cost, the telescoped headband assembly 36 may be dispensed with in favor of a one-piece headband assembly where adjustment is effected only via the locking knob assembly 35.

A pair of first tension springs 46 is connected to both the ear protector attachment and the first ear cover support strut assembly for urging the first ear cover support strut assembly towards a wearer's head. A pair of second tension springs 48 is connected to both the ear protector attachment and the second ear cover support strut assembly for urging the second ear cover support strut assembly towards the wearer's head. Each of the first ear cover support strut assembly and the second ear cover support strut assembly includes a pair of first telescopic strut members 40 connected to the ear protector attachment. A pair of second telescopic strut members 42 is connected between the first telescopic strut member 40 and one of the ear cover assemblies. A pair of strut lock members 44 are received in the second telescopic strut member 42 and are used for locking the first telescopic strut member 40 and the second telescopic strut member 42 in a selected longitudinal adjustment.

To use the eye, ear, and respiration protection apparatus 10 of the invention, the strut lock members 44 are loosened so that the first telescopic strut members 40 and the second telescopic strut members 42 can be adjusted longitudinally so that the nose and mouth mask 14 is snugly on the wearer's face and the ear cover assemblies are properly located on the wearer's ears. Then the strut lock members 44 are tightened. The overhead band assembly is then adjusted by use of the locking knob 35 and/or the telescoped arrangement between headband portions 37 and 39 so that the overhead band 36 fits snugly and comfortably on the wearer's head.

The eye goggle assembly 20 can include lenses that are made of clear or tinted tempered glass. The air filter elements 16 can be OSHA approved for use with chemicals, solvents, and/or particulates. The air filter elements 16 can be in the form of standard replaceable cartridges. To provide an effective and soft interface between the nose and mouth mask 14 and a wearer's face, a silicone rubber skirt 51 preferably is provided on the edge of the nose and mouth mask 14 (see FIGS. 2, 3, and 5). Similarly, a silicone rubber skirt surround 53 may be provided on the peripheral edge of the eye goggle assembly 20.

If desired, the ear protector assembly 22 can be removed and replaced with an adjustable strap when the wearer will not be in an environment that is hazardous to the ears. Similarly, the eye goggle assembly 20 can be removed when the environment of use is not hazardous to the eyes. In environments in which communication between a wearer and others may be difficult, the eye, ear, and respiration protection apparatus 10 of the invention can also be equipped with a conventional voice electronic transmitter 49 and receiver 50 (e.g. radio, telephone, etc.). In addition, the eye, ear, and respiration protection apparatus 10 can also be equipped with a work light which can be powered by a belt-worn battery pack. If desired, the eye, ear, and respiration protection apparatus 10 can includes an input jack for a tape or compact disc player. A self-contained AM/FM receiver can also be provided.

Turning now to the alternatively preferred embodiment of the invention shown in FIGS. 7 thru 10, the same reference signs are used that correspond to like elements shown in the other Figures. In addition, a rearward headband 60 is provided. More specifically, the overhead band 36 supports the weight of the eye, ear, and respiration protection apparatus 10, and the rearward headband 60 is generally in a horizontal orientation and pulls the nose and mouth mask 14 and the eye goggle assembly 20 onto the wearer's face. The overhead band 36 includes a band ring end 66 attached to the exterior of a first of a pair of band locking units 62 and includes a serrated portion received in an interior portion of a second of the pair of band locking units 62. In like manner, the rearward headband 60 includes a band ring end 66 attached to the exterior of the second of the pair of band locking units 62 and includes a serrated portion received in the interior of the first of the pair of band locking units 62. With this arrangement of the overhead band 36, the rearward headband 60, and the band locking units 62, the wearer has independent control of the tension and orientation angle of each of the overhead band 36 and the rearward headband 60. Each of the overhead band 36 and the rearward headband 60 includes serrations 64.

Each of the pair of band locking units 62 includes a cylinder 68 which includes a top cylinder end and a bottom cylinder end. The cylinder 68 includes exterior threads 69. A piston 70 is received in the cylinder 68. The piston 70 includes a finger pressure button end 72 and the cylinder 68 includes a head band pressing end 74. A spring 83 is connected to bottom cylinder end. A serration engager 78 is connected to the spring 83, and an internally threaded locking ring 80 screwed onto the exterior threads 69 of the cylinder 68. Each locking ring 80 includes a flange 82 to permit the respective band locking unit 62 to be retained by a respective ear cover assembly.

More specifically, the spring 83 provides a locking pressure on the serration engager 78 to engage a positioned serration 64 of a respective headband. Through the headband, pressure is transmitted to the head band pressing end 74 of the cylinder 68. This force is transmitted through the piston 70 to the finger pressure button end 72 which is retained by the locking ring 80. In this way, and as will be more fully explained below, the respective headband is clamped in the respective band locking unit 62.

Figure 9:
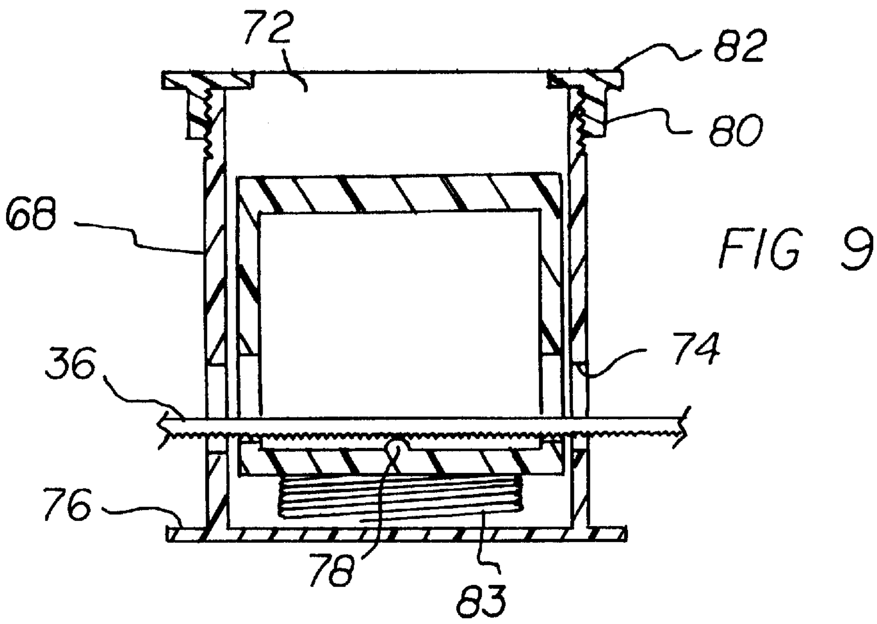
FIG. 9 is a cross-sectional view in elevation taken along line 9—9 in FIG. 8.
Figure 10:
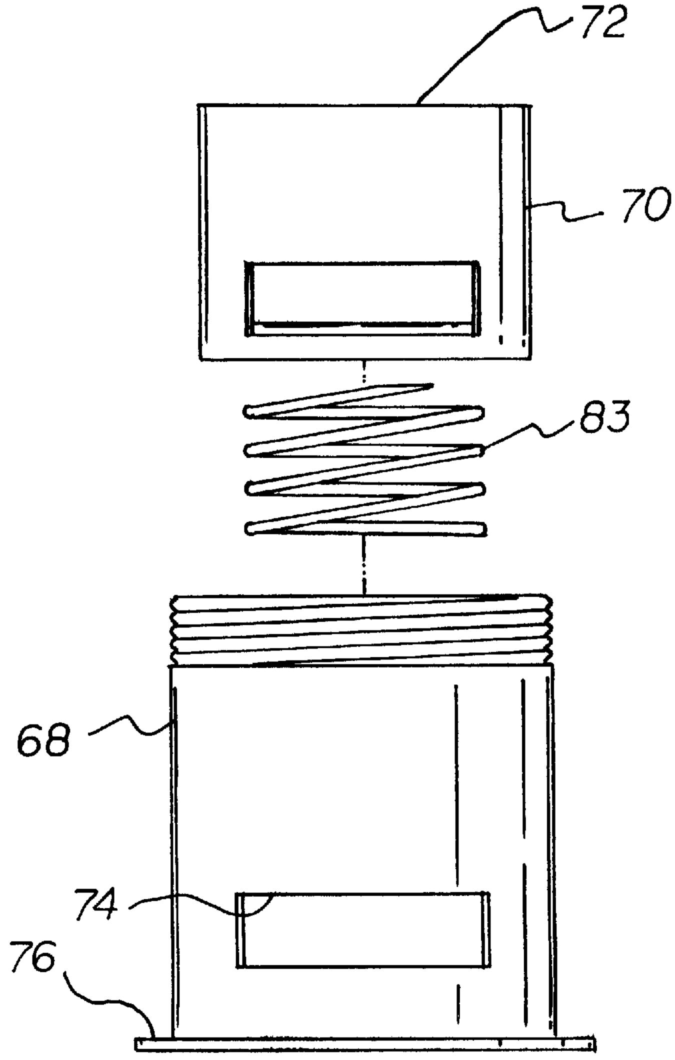
FIG. 10 is an exploded assembly view of the band locking unit of FIGS. 8 and 9.

Each cylinder 68 and each piston 70 includes headband reception channels for receiving a portion of a respective head band (see FIG. 10). The upper edges of the reception channels in the cylinder 68 define the headband pressing end 74. The serration engager 78 is in the form of a triangular or rounded tooth whose apex fits in between two serrations 64. When the finger pressure button end 72 is released, the spring 83 urges piston 70 upwardly as viewed in FIGS. 8–10 against the retaining flange 82 whereupon the headband portion received in the reception channels is stabilized or locked in its adjusted position by frictional engagement between the upper edges defined by the headband pressing end 74 and the headband 36 per se.

The finger pressure button end 72 of the piston 70 is recessed under the outside edge of the locking ring 80 so that inadvertent release of the piston 70 on the headband is avoided. However, to intentionally release a headband strap from its locked position in a respective band locking unit 62, one need only first apply a suitable force on the finger pressure button end 72 of the piston 70 sufficient to cause the spring 83 to be compressed and to align the headband reception channels, substantially as shown in FIG. 9. Then, the tension of the respective headband is adjusted, and the piston 70 is released to once again lock the headband in the newly adjusted position. Such force may easily be applied by one's finger in an inward direction with respect to the side of the head as viewed in FIG. 7, for example, i.e. perpendicular to the plane of the drawing.

The headbands are preferably made of plastic and are easily replaced if the serrations 64 wear excessively. Generally, the shape of the serration engager 78 is complimentary to the serrations 64 of the head bands.

Figure 7:
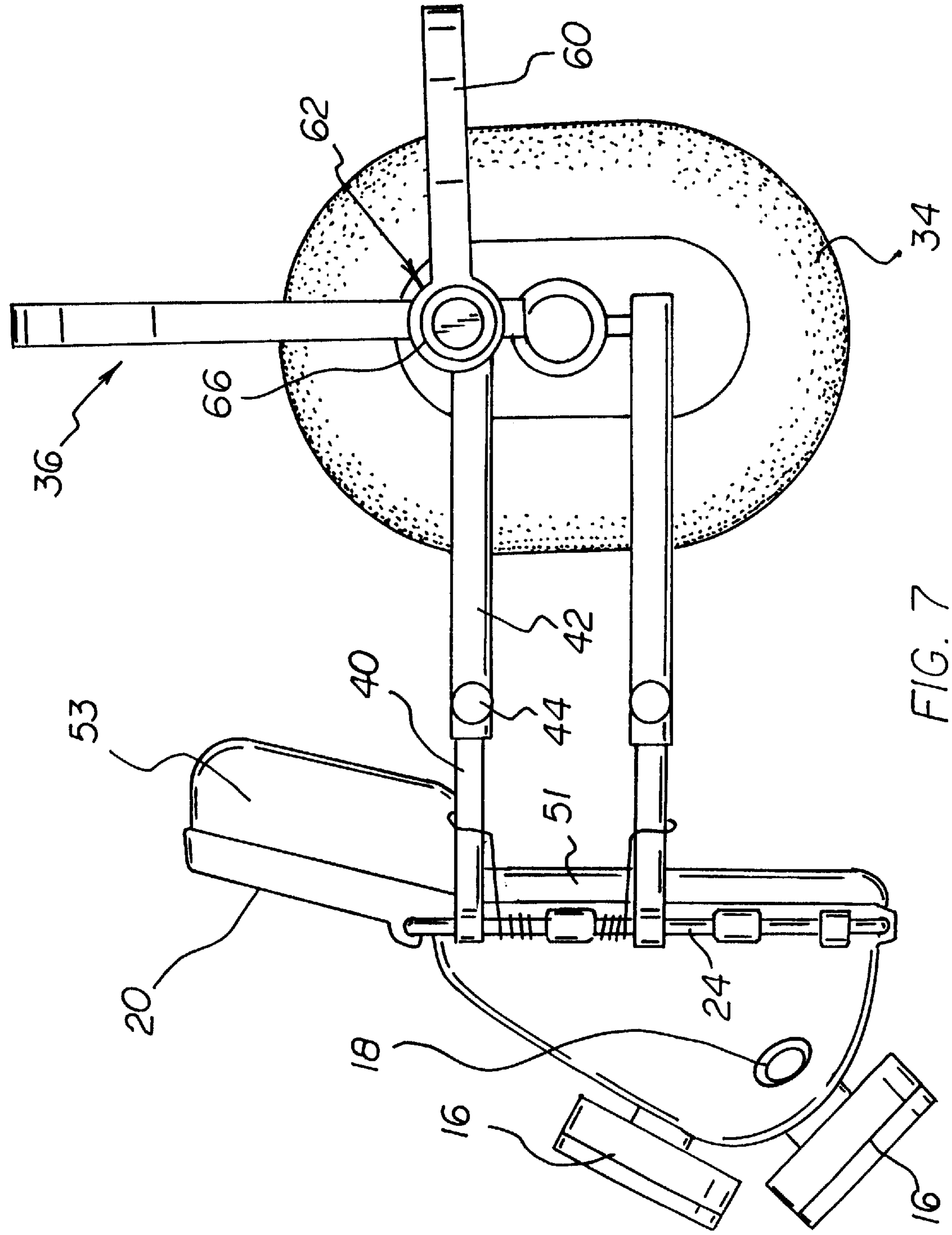
FIG. 7 is a side view showing a second embodiment of the invention which includes two head straps, one for the top of a wearer's head, and one for the back of the wearer's head.
Figure 8:
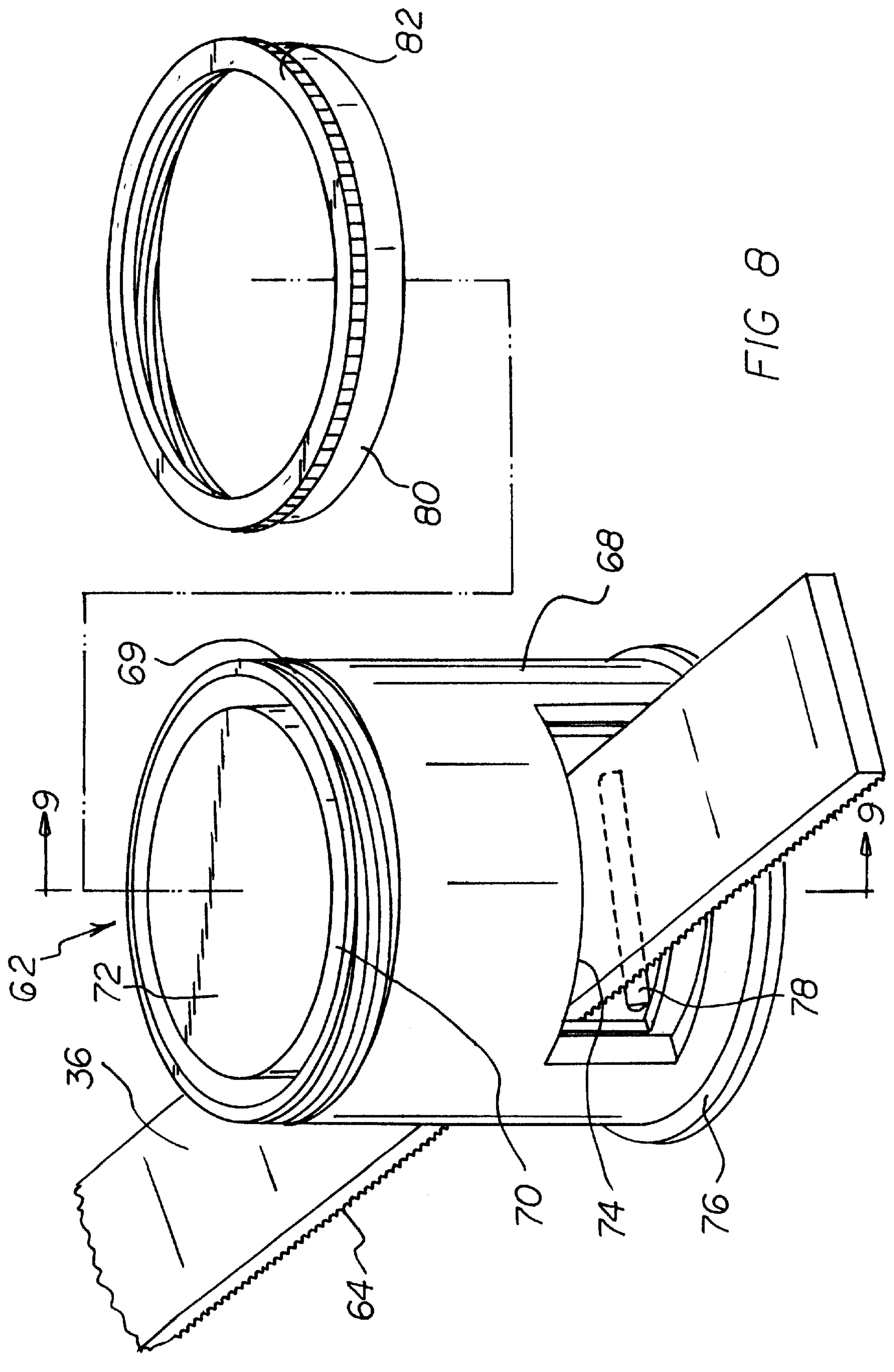
FIG. 8 is a partially exploded perspective view of one of a pair of band locking units used for locking the band worn on the top of the wearer's head and for the band worn on the back of the wearer's head.

As shown in the alternatively preferred embodiment of FIG. 7, the telescopic arms 40 may be mounted higher on the mask attachment wires 24 (relative to the first embodiment) to provide for a more optimal fit, if desired.

The components of the eye, ear, and respiration protection apparatus of the invention can be made from inexpensive and durable metal, plastic, rubber and glass materials.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing a new and improved eye, ear, and respiration protection apparatus that is low in cost, relatively simple in design and operation, and which may advantageously be used without covering substantial portions of the wearer's forehead and neck. With the invention, an eye, ear, and respiration protection apparatus is provided which uses linear struts to connect a nose and mouth mask to an ear protector assembly. With the invention, an eye, ear, and respiration protection apparatus provides that the linear struts between the nose and mouth mask and the ear protector assembly are adjustable to accommodate different size heads. With the invention, an eye, ear, and respiration protection apparatus provides that the ear protector assembly is adjustable laterally to accommodate different head sizes. With the invention, an eye, ear, and respiration protection apparatus is provided which includes one headstrap that extends over the wearer's head and includes another headstrap that extends behind the wearer's head. With the invention, an eye, ear, and respiration protection apparatus provides push buttons locks both to release the headstraps when adjustments are needed and to lock the headstraps after the adjustments have been made.

Thus, while the present invention has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

Hence, the proper scope of the present invention should be determined only by the broadest interpretation of the appended claims so as to encompass all such modifications as well as all relationships equivalent to those illustrated in the drawings and described in the specification.

What is claimed as being new and desired to be protected by LETTERS PATENT of the United States is as follows:

1. An eye, ear, and respiration protection apparatus, comprising in combination:

a respirator assembly which includes a nose and mouth mask, an air filter element connected to said nose and mouth mask, and an air flow valve connected to said nose and mouth mask, eye protector attachment means connected to said nose and mouth mask, an eye goggle assembly connected to said eye protector attachment means, ear protector attachment means connected to said nose and mouth mask, and an ear protector assembly connected to said ear protector attachment means, wherein said eye protector attachment means and said ear protector attachment means are comprised of a single attachment wire connected to said nose and mouth mask, wherein said eye goggle assembly includes goggle connector portions connected to said attachment wire, and wherein said goggle connector portions are rotatable around said attachment wire, and wherein said ear protector attachment means includes connection portions adjustably connected to said attachment wire.

2. The apparatus of claim 1, further including:

a rubber skirt on an edge portion of said nose and mouth mask.

3. The apparatus of claim 1, further including:

a rubber skirt surround on a peripheral edge portion of said eye goggle assembly.

4. The apparatus of claim 1 wherein said ear protector assembly includes:

a first ear cover support strut assembly connected to said ear protector attachment means, a first ear cover assembly connected to said first ear cover support strut assembly, a second ear cover support strut assembly connected to said ear protector attachment means, a second ear cover assembly connected to said second ear cover support strut assembly, and an overhead band connected between said first ear cover assembly and said second ear cover assembly.

5. The apparatus of claim 4 wherein said overhead band is connected to said first ear cover assembly and said second ear cover assembly.

6. The apparatus of claim 5 wherein said overhead band is pivotally connected to said first ear cover assembly and said second ear cover assembly.

7. An eye, ear, and respiration protection apparatus, comprising:

a respirator assembly which includes a nose and mouth mask, an air filter element connected to said nose and mouth mask, and an air flow valve connected to said nose and mouth mask, eye protector attachment means connected to said nose and mouth mask, an eye goggle assembly connected to said eye protector attachment means, ear protector attachment means connected to said nose and mouth mask, and an ear protector assembly connected to said ear protector attachment means, wherein said ear protector assembly includes:

a first ear cover support strut assembly connected to said ear protector attachment means, a first ear cover assembly connected to said first ear cover support strut assembly, a second ear cover support strut assembly connected to said ear protector attachment means, a second ear cover assembly connected to said second ear cover support strut assembly, and an overhead band connected between said first ear cover assembly and said second ear cover assembly, the apparatus further including:

a rearward headband connected between said first ear cover assembly and said second ear cover assembly, wherein each of said overhead band and said rearward headband includes serrations, further including:

a pair of band locking units wherein a first of said band locking units is connected to said first ear cover assembly, and wherein a second of said band locking units is connected to said second ear cover assembly, wherein each of said overhead band and said rearward headband includes a band ring end connected to an outer portion of one of said pair of band locking units, and each of said overhead band and said rearward headband includes serrations which are locked by interior locking portions of the opposite one of said pair of band locking units.

8. The apparatus of claim 7 wherein each of said pair of band locking units includes:

a cylinder which includes a top cylinder end and a bottom cylinder end, wherein said cylinder includes exterior threads, a piston received in said cylinder, wherein said piston includes a finger pressure button end and a head band pressing end, a spring connected to bottom cylinder end, a serration engager connected to said spring, and an internally threaded locking ring screwed onto said exterior threads of said cylinder.

9. An eye, ear, and respiration protection apparatus, comprising:

a respirator assembly which includes a nose and mouth mask, an air filter element connected to said nose and mouth mask, and an air flow valve connected to said nose and mouth mask, eye protector attachment means connected to said nose and mouth mask, an eye goggle assembly connected to said eye protector attachment means, ear protector attachment means connected to said nose and mouth mask, and an ear protector assembly connected to said ear protector attachment means, wherein said ear protector assembly includes:

a first ear cover support strut assembly connected to said ear protector attachment means, a first ear cover assembly connected to said first ear cover support strut assembly, a second ear cover support strut assembly connected to said ear protector attachment means, a second ear cover assembly connected to said second ear cover support strut assembly, and an overhead band connected between said first ear cover assembly and said second ear cover assembly, and wherein said overhead band includes:

a first telescopic band member connected to said first ear cover assembly, and a second telescopic band member connected to said second ear cover assembly, wherein said first telescopic band member telescopically receives said second telescopic band member.

10. The apparatus of claim 9, further including:

a first tension spring connected to both said ear protector attachment means and said first ear cover support strut assembly for urging said first ear cover support strut assembly towards a wearer's head, a second tension spring connected to both said ear protector attachment means and said second ear cover support strut assembly for urging said second ear cover support strut assembly towards the wearer's head.

11. An eye, ear, and respiration protection apparatus, comprising:

a respirator assembly which includes a nose and mouth mask, an air filter element connected to said nose and mouth mask, and an air flow valve connected to said nose and mouth mask, eye protector attachment means connected to said nose and mouth mask, an eye goggle assembly connected to said eye protector attachment means, ear protector attachment means connected to said nose and mouth mask, and an ear protector assembly connected to said ear protector attachment means, wherein said ear protector assembly includes:

a first ear cover support strut assembly connected to said ear protector attachment means, a first ear cover assembly connected to said first ear cover support strut assembly, a second ear cover support strut assembly connected to said ear protector attachment means, a second ear cover assembly connected to said second ear cover support strut assembly, and an overhead band connected between said first ear cover assembly and said second ear cover assembly, and wherein each of said first ear cover support strut assembly and said second ear cover support strut assembly includes:

a first telescopic strut member connected to said ear protector attachment means, a second telescopic strut member connected between said first telescopic strut member and one of said ear cover assemblies, and a strut lock member, received in said second telescopic strut member, for locking said first telescopic strut member and said second telescopic strut member in a selected longitudinal adjustment.

* * * * *